Feb. 24, 1959 SHIGENOBU KURAMOTO Plant Pat. 1,813
ROSE PLANT
Filed April 7, 1958
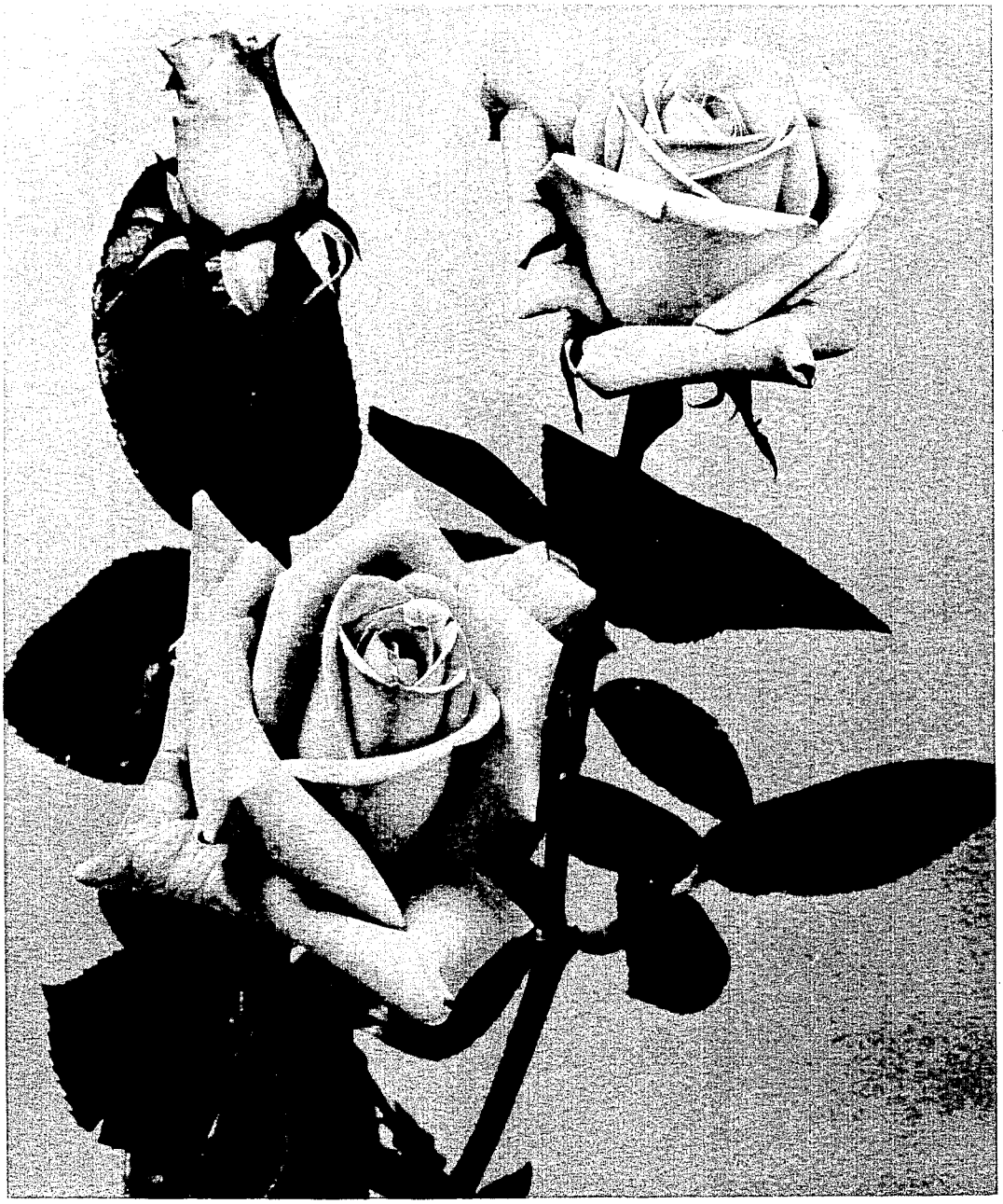
INVENTOR
Shigenobu Kuramoto
By Orville M. Kile
Plant Patent Agent United States Patent Office Plant Pat. 1,813
Patented Feb. 24, 1959

1,813

ROSE PLANT

Shigenobu Kuramoto, San Lorenzo, Calif.

Application April 7, 1958, Serial No. 727,014

1 Claim. (Cl. 47—61)

My present invention is an improved variety of hybrid tea rose plant in the red-flowered class. It originated as a sport of Pink Delight (unpatented) and has many of the qualities of its parent. The chief differences lie in its easier growth; more prolific production of good blooms; and glossier, better-textured foliage; as well as production of a darker, more fragrant flower.

I have asexually reproduced the new variety through several generations by means of budding, at our nurseries in San Lorenzo, California, and the distinguishing characteristics appear to be permanent.

Accompanying illustrations show three specimens of the rose in various stages of opening, together with stems and foliage—all in as nearly the true coloring as the artist was able to make them with color photography. Allowance must be made for distortions in coloring, particularly of some of the foliage, and reliance placed upon the color description.

In the following detailed description, color plate references indicate Ridgway's Color Standards and Nomenclature. Other reference to color indicates the ordinary dictionary meaning of the term.

*The plant*

Growth habit: A very strong and vigorous grower.

Form: Compact bush. Can be grown to 5 or 6 feet in height.

Disease resistance: Grown at our nurseries under the same conditions as its parent, the new variety is less subject to mildew; also grown under the same conditions as Red Delight, the new variety is considerably less subject to mildew.

Blooming habit: Continuous and very prolific bloomer.

Foliage:

*Quantity.*—Abundant.

*Type.*—Pinnately compound, mostly three to five leaflets.

*Shape.*—Leaflets oval with rounded base and acuminate apex.

*Appearance.*—Glossy.

*Veination.*—Has many more veins than found in the foliage of most rose plants.

*Edge.*—Finely serrated.

*Color.*—Approximately Elm Green (Pl. XVII). Under surface, approximately Cress Green (Pl. XXXI).

*Size.*—Terminal leaflets approximately 2½ inches long by 1½ inches wide.

*Texture.*—Moderately heavy; fine-textured.

*Rachis.*—Slender.

*Stipules.*—Clinging, except for long points.

Stems:

*Strength.*—Strong and sturdy, holding flower upright.

*Color.*—Between Grass Green (Pl. VI) and Forest Green (Pl. XVII).

*Thorns.*—Numerous; sharp; downward-pointing; whitish-green.

*The bloom*

Bud:

*Form.*—At first slightly pointed, becoming long urn-shaped.

*Size.*—Just as bud begins to become urn-shaped, the length is from 1½ to 1¾ inches.

*Sepals.*—Mostly simple.

*Calyx.*—Broad funnel-shaped.

*Peduncle.*—Medium length, permitting foliage to come rather close to flower; sturdy; same color as stems.

*Color.*—Similar to that of Red Delight (unpatented) but slightly lighter. Some specimens are almost true Rose Color (Pl. XII); others darker, with a tinge of Tyrian Rose (Pl. XII), the latter growing more evident as the bud opens.

Flower:

*Borne.*—Singly, on long stems.

*Size.*—Medium. Never opens wide, but it flattened would measure 3 to 3½ inches in diameter.

*Form.*—Full, rounded, with tight center, which form is retained. Has the appearance of heavy petalage.

*Color.*—At first the color is approximately same as the buds. In most instances, two or three of the outer petals have a vertical white streak varying in width. As the bloom ages, it becomes Tyrian Rose (Pl. XII), and much later is a beautiful purple—from Purple (Pl. XI) to Rood's Violet (XI) in the center. At this stage the edge of the inner surface of the petals appears velvety.

*Petalage.*—Double, with an average of 35 to 45 petals.

*Fragrance.*—Intense and delightful.

*Lasting quality.*—Lasts exceptionally well on bush and as cut flower.

Petals:

*Quantity.*—Varies greatly in different specimens and at different seasons of the year, numbering from 30 to 75.

*Appearance.*—Smooth, and silky.

*Form.*—Almost round, with slight notch or point at tip. Rather deeply cupped.

*Edge.*—Whole.

*Texture.*—Silky, with tips of inner surface velvety.

*Size.*—Outer petals approximately 1½ by 1½ inches.

*Comparisons*

The varieties which my new variety most resembles are Pink Delight and Red Delight. The principal differences are as follows:

Compared with Pink Delight, my new variety:

(1) Grows more easily.
(2) Produces more blooms.
(3) Is not as subject to mildrew when grown under same conditions.
(4) Has foliage of finer and more substantial texture, and greater veination.
(5) Has flowers much darker in color.
(6) Has flowers much more fragrant.
(7) Has flowers with many more petals.

Compared with Red Delight, my new variety:

(1) Grows very much more easily.
(2) Produces more blooms.
(3) Is much less subject to mildew when grown under the same conditions.
(4) Has bigger buds.
(5) Produces finer textured foliage, with fuller veination.
(6) Has flowers which are at first slightly lighter in color but turn much darker.
(7) Has flowers with many more petals.

(8) Has flowers with much more fragrance.
(9) Petals of flowers open wider.

Having thus disclosed my discovery, I claim:

The new and distinct variety of hybrid tea rose plant, substantially as herein shown and described, characterized particularly by its easy, mildew-resistant growth; fine-textured and numerous-veined foliage; large buds and prolific production of very full, exceedingly fragrant rose-red flowers which later turn much darker.

No references cited.